United States Patent [19]

Weiss et al.

[11] Patent Number: 5,719,319
[45] Date of Patent: Feb. 17, 1998

[54] PROCESS FOR THE PREPARATION OF A CREATINE OR CREATINE MONOHYDRATE

[75] Inventors: Stefan Weiss; Helmut Krommer, both of Trostberg, Germany

[73] Assignee: SKW Trostberg Aktiengesellschaft, Trostberg, Germany

[21] Appl. No.: 677,073

[22] Filed: Jul. 9, 1996

[30] Foreign Application Priority Data

Jul. 18, 1995 [DE] Germany ............... 195 26 236.0

[51] Int. Cl.[6] ..................................... C07C 241/00
[52] U.S. Cl. ............................................. 562/560
[58] Field of Search .................................. 562/560

[56] References Cited

U.S. PATENT DOCUMENTS

| | | | |
|---|---|---|---|
| 1,967,400 | 7/1934 | Fischl | 562/560 |
| 2,620,354 | 12/1952 | Vassel | 562/560 |
| 2,654,779 | 10/1953 | Vassel | 562/560 |
| 3,036,087 | 5/1962 | Anatol | 560/562 |

FOREIGN PATENT DOCUMENTS

| | | |
|---|---|---|
| 494918 | 3/1930 | Germany . |
| 55-4349 | 1/1980 | Japan . |
| 937931 | 9/1963 | United Kingdom . |

OTHER PUBLICATIONS

Mortimer, "Chemistry A Conceptual Approach," pp. 460–462 & 500–515, 1967.
Morrison, "Organic Chemistry," 2nd Ed., pp. 582–583, 1966.
King, J. Chem. Soc., pp. 2374–2377, 1930.
Chemical Abstracts, vol. 99, No. 19, Nov. 7, 1983, p. 653 34–Amino Acids, Peptides, and Proteins, abstract no. 158796t.

*Primary Examiner*—Michael L. Shippen
*Attorney, Agent, or Firm*—Felfe & Lynch

[57] ABSTRACT

Disclosed is a process for the preparation of creatine or creatine monohydrate, wherein cyanamide is reacted with sodium or potassium sarcosinate in water or in a mixture of water and en organic solvent at a temperature of from 20 to 150° C. and a pH value of from 7.0 to 14.0.

By means of the process according to the present invention, creatine or creatine monohydrate can be prepared in good yields of from 60 to 90% by weight and with very high purity.

20 Claims, No Drawings

PROCESS FOR THE PREPARATION OF A CREATINE OR CREATINE MONOHYDRATE

BACKGROUND OF THE INVENTION

The present invention is in a process for the preparation of creatine or creatine monohydrate by the reaction of cyanamide with sodium or potassium sarcosinate.

Creatine occurs in muscle tissue and, as creatine phosphate, is an energy reserve of muscles. For this reason, creatine is used as a nutritional supplement, especially in the field of sport, creatine thereby usually being administered as creatine monohydrate. Creatine can be obtained from biological material, for example meat waste, which is, however, technically very laborious and is questionable for hygienic reasons.

According to the prior art, the preparation of creatine takes place by the reaction of cyanamide with sarcosine (cf., Ullmann's Encyclopedia of Industrial Chemistry, 5th edition, Volume A 12, 552, VCH-Verlagsgesellschaft, Weinheim, 1987; Strecker, Jahresbericht über die Fortschritte der Chemie, 1868, 686 Anm. D; Volhard, Zeitschrift for Chemie, 1869, 318).

A decisive disadvantage in the case of the preparation of creatine or creatine monohydrate from sarcosine and cyanamide is that sarcosine is a very expensive starting material and, in the case of the use of the expensive sarcosine, satisfactory results cannot be achieved.

Therefore, it is an object of the present invention to develop of process for the preparation of creatine or creatine monohydrate which does not suffer from the above-mentioned disadvantages of the prior art but rather makes possible the preparation of creatine or creatine of a good purity in an economically useful yield.

THE INVENTION

The present invention is in a process for the preparation of creatine or creatine monohydrate, wherein cyanamide is reacted with sodium or potassium sarcosinate in water or in a mixture of water and an organic solvent at a temperature of from 20° to 150° C. and at a pH value of from 7.0 to 14.0.

Surprisingly, it has been found that by the process of the invention the desired reaction product is obtained in good yields and in a very high purity. That a high purity, high yield product can be obtained is all the more surprising because it is known that cyanamide dimerizes in the alkaline range to give dicyandiamide, the maximum reaction rate being at about a pH of 9.6. Furthermore, above a pH of 9, in addition to the formation of dicyandiamide, at the same time an addition of water to cyanamide also results with the formation of urea. Finally, it is also known that under alkaline conditions in the case of heating with water creatine decomposes, whereby, inter alia, sarcosine, urea and methylhydantoin form. Accordingly, it could not have been expected that, by the process of the present invention, one could obtain good yields and high purities of the desired product.

It is especially surprising that even technical solutions of sodium and potassium sarcosinate, which only have a purity of 85 to 90% by weight and contain about 10% by weight of methyliminodiacetic acid in the form of its salts as impurity, can be used for the preparation of creatine or creatine monohydrate with the above-mentioned advantages.

Thus, in the case of the process according to the present invention, the reaction components cyanamide and sodium or potassium sarcosinate are reacted at a reaction temperature of from 20° to 150° C. and preferably of from 50° to 100° C. optionally under pressure.

It is important for the process according to the present invention that the reaction is carried out in the alkaline range from pH 7.0 to 14.0 and preferably from 9.0 to 10.0. The appropriate pH value is preferably adjusted with the aid of an inorganic or organic acid. An example of a suitable inorganic (mineral) acid, is hydrochloric acid. Examples of suitable organic acids are sarcosine, acetic acid or formic acid. However, instead of these, the pH value adjustment can readily also take place with aliphatic mono-, di- or polycarboxylic acids and especially also with aromatic carboxylic acids, as well as aliphatic or aromatic sulphonic acids.

In the scope of the present invention, it is also possible to carry out the pH value adjustment with bases, especially sodium hydroxide or potassium hydroxide, if it is intended to operate in the upper range of the disclosed pH value.

The mole ratio of cyanamide to sodium or potassium sarcosinate can be varied in wide limits and is preferably adjusted to a value of from 1:4 to 4:1. In a preferred embodiment, the cyanamide and the sodium or potassium sarcosinate are used in substantially equimolar amounts, for example 0.9:1 to 1.25:1.

The reaction can be conducted, for example, in such a manner that an aqueous solution of sodium or potassium sarcosinate is adjusted with an acid or alkaline lye to the desired pH value and cyanamide is added thereto in the form of an aqueous solution, for example as a 50% aqueous solution, or in solid crystalline form. However, it is possible to proceed in such a manner that pH value adjustment only takes place during the addition of the cyanamide.

Alternatively, cyanamide and sodium or potassium sarcosinate can also be introduced simultaneously into the reaction vessel, the pH value desired thereby being adjusted simultaneously with the help of an acid or base.

As a reaction vessel, there can be used, inter alia, a stirrer container or a loop reactor. The use of a loop reactor is especially recommended when the addition of cyanamide into the sodium or potassium sarcosinate and the adjustment of the pH value takes place simultaneously.

According to a preferred embodiment of the process according to the present invention, the sodium or potassium sarcosinate is used in the form of a appropriate technical aqueous solution, which preferably has a concentration of from 35 to 40% by weight and a degree of purity of about 85 to 90% by weight. In contradistinction to sarcosine, the technical aqueous sodium sarcosinate solutions are relatively inexpensive since it is hereby a question of a large-scale technical product.

The reaction according to the present invention proceeds in a very simple manner in a water or aqueous suspension. However, it can also be carried out in an aqueous organic phase, for example in the presence of an aliphatic alcohol containing up to 5 carbon atoms. The alcohol is preferably methanol or ethanol. The use of an organic solvent permits a simple adjustment of the desired reaction temperature in that the reaction mixture is heated to the reflux temperature.

After the reaction has taken place which, as a rule, is for a 2 to 5 hour period, the solid reaction product is isolated by the use of conventional separating equipment such as for example, a centrifuge, filter press or suction filtration device. For purification or preparation of very pure creatine or creatine monohydrate, the reaction product can be after-treated with cold or hot, for example by washing with water or suspending in, water. The reaction product can also be recrystallized from water.

The subsequent drying of the moist product can take place, for example, with the help of known convection or contact driers. As driers, there can be used, for example, chamber driers, tunnel driers, belt driers, rack driers, nozzle driers, flow driers, fluidised bed driers or drum driers.

For the preparation of anhydrous creatine, the product is so dried that the water content lies below 1% by weight. This can be achieved, for example, by drying in a vacuum at 80° C.

For the preparation of creatine monohydrate, the drying procedure is discontinued at a water content of about 12.1% by weight or the drying parameters are so chosen that the water content does not fall below about 12.1% by weight. Creatine monohydrate has a theoretical water content of 12.08% by weight. Surprisingly, it has been found that the drying of moist creatine can be specifically so carried out that creatine monohydrate is obtained. For this purpose, drying in a rack drier at 40° C. and 15 to 20 mbar pressure is recommended or in a drum drier at 50° C. and 180 to 200 mbar pressure.

By the process according to the present invention, creatine or creatine monohydrate can be prepared in yields of 60 to 90% by weight and with very high purity of up to 100%, even when starting from technical sodium or potassium sarcosinate solutions with a purity of only 85 to 90% by weight. Since the space/time yields of the process according to the present invention are very good, it is extremely useful for conducting technical scale production.

The following Examples further are given for the purpose of illustrate the present invention.

EXAMPLE 1

4625 g (16.7 moles) of 40% by weight technical aqueous sodium sarcosinate solution were used. With external cooling with cold water and vigorous stirring, a pH value of 9.6 (at 20° C.) was adjusted with concentrated hydrochloric acid. The reaction mixture was heated to 80° C. 1548 g (18.4 moles) of a 50% by weight aqueous cyanamide solution (SKW cyanamide L 500) were introduced in the course of 90 minutes with strong stirring and uniformly at an internal temperature of 80° to 85° C. After ending of the cyanamide addition, the reaction mixture was further stirred for 2 hours at an internal temperature of 80° C. The reaction mixture was cooled and stirred for 4 hours with water cooling. The crystalline, readily filterable reaction product was filtered off with suction and washed chloride-free by washing three times with, in each case, 1250 ml of water. Subsequently, after-washing was again carried out with 1250 ml of water with a temperature of 40° C. The product was dried in a vacuum drying cabinet at 40° C. and 20 mbar pressure. The yield of creatine monohydrate was 1822 g (73.3%, referred to sodium sarcosinate). Content (HPLC): 88.1% creatine (calculated 87.9%).

EXAMPLE 2

277.7 g (1 mole) of a technical 40% by weight aqueous sodium sarcosinate solution were used. A pH value of 9.6 (at 20° C.) was adjusted with concentrated hydrochloric acid and heated to 95° C. Subsequently, 105.1 g (1.25 mole) of a technical 50% by weight aqueous cyanamide solution were added thereto with intensive stirring in such a manner that the internal temperature did not exceed 95° C. After ending of the cyanamide addition, further heating was carried out for 1 hour at 95° C. The reaction mixture was then cooled to 15° C. the crystalline precipitate was filtered off with suction and washed chloride-free by washing twice with, in each case, 120 ml of water. The residue was recrystallized from water and dried at 80° C. and 20 mbar. The yield of creatine was 73.4 g (56% of theory). The content determination by means of HPLC gave a content of 100% (creatine monohydrate obtainable pure in chemical commerce was used as standard).

EXAMPLE 5

493.2 g (1.78 moles) of a technical 40% by weight aqueous solution of sodium sarcosinate and 214 g of water was placed in a four-necked flask equipped with a stirrer, thermometer and pH meter. At 20° C., a pH value of 9.93 was adjusted with acetic acid, while stirring. The temperature was then adjusted 70° C. With intensive stirring, 138.2 g (1.65 moles) of a 50.2% by weight aqueous solution of cyanamide (SKW cyanamide L 500) were uniformly added dropwise with the help of a dosing pump over the course of 90 minutes at an internal temperature of 70° to 72° C. After ending of the cyanamide addition, the reaction mixture was further stirred for 60 minutes at an internal temperature of 70° C. After cooling to 15° C., the crystalline, readily filterable precipitate was filtered off with suction and, without washing, suspended in 330 g of water. The suspension was stirred for 1 hour at 20° C. The precipitate was filtered off with suction and subsequently, without washing, dried at 30° C. in a vacuum drying cabinet for 16 hours. The yield was 177.7 g (72.2% of theory) of creatine monohydrate.

content (HPLC): 88.0% creatine (calculated 87.9%)

crestinine (HPLC): <200 ppm dicyandiamide: 220 ppm water (infrared drying weight at 105° C.: 11.9% (calculated 12.08%)

EXAMPLE 4

462.5 g (1.67 moles) of a technical 40% by weight aqueous sodium sarcosinate solution and 200 g of water were take. A pH value of 9.81 (at 20° C.) was adjusted with concentrated 98% by weight formic acid. The reaction mixture was heated to 50° C. 138.2 g (1.65 moles) of SKW cyanamide L 500 (technical aqueous cyanamide solution with a content of 50.2% by weight) were added uniformly with vigorous stirring at an internal temperature of 50° to 52° C. over the course of 3 hours. The reaction mixture was further stirred for 1 hour at an internal temperature of 50° C. Subsequently, the reaction product was filtered off with suction and, without washing, suspended in 330 g of water. The suspension was stirred for 2 hours at 20° C. It was then filtered off with suction and the residue washed twice with 100 ml of water. After drying in a vacuum at 30° C. and 20 mbar pressure, there were obtained 165.2 g (67.1% of theory) creatine monohydrate.

content: 88.12% (HPLC, calculated 87.9%)

water: 12.1% (IR drying weight, 105° C.; calculated 12.08%)

EXAMPLE 5

674.5 g (2.43 moles) of 40% by weight aqueous sodium sarcosinate solution were taken and a pH value of 8.5 adjusted at 70° C. with 99% by weight acetic acid. After the addition of 500 ml methanol, 491.1 g (2.92 moles) of a 25% by weight aqueous cyanamide solution were added thereto with vigorous stirring at reflux temperature in the course of 2 hours. After ending of the addition of the cyanamide solution, the reaction mixture was further stirred for 2 hours under reflux while stirring. After cooling to 15° C., the crystalline precipitate was filtered off with suction, washed twice with, in each case, 250 ml of water and subsequently recrystallised from water. After drying in a vacuum drying cabinet at 80° C. and 15 mbar pressure, there were obtained 176.7 g (48.8% by weight) of anhydrous creatine.

Purity (HPLC): 99.9%

EXAMPLE 6

Analogously to Example 1, a 40% by weight aqueous potassium sarcosinate solution was reacted with cyanamide. The yield of pure creatine monohydrate was 1875 g (75.3% of theory).

It will be understood that the specification and examples are illustrative but not limitative of the present invention and that other embodiments within the spirit and scope of the inventions will suggest themselves to those skilled in the art.

We claim:

1. A process for the preparation of creatine or creatine monohydrate, comprising: reacting cyanamide with sodium or potassium sarcosinate in water, or in a mixture of water and an organic solvent, at a temperature of from 20° to 150° C. and a pH value of from 7.0 to 14.0.

2. The process of claim 1 wherein the temperature is from 50° to 100° C.

3. The process of claim 1 wherein the pH value is 9.0 to 10.0.

4. The process of claim 1 wherein the pH value is adjusted with an inorganic acid.

5. The process of claim 4 wherein the inorganic acid is hydrochloric acid.

6. The process of claim 1 wherein the pH value is adjusted with an organic acid.

7. The process of claim 6 wherein the organic acid is at least one of sarcosine, acetic acid, and formic acid.

8. The process of claim 1 wherein the mole ratio of cyanamide to sodium or potassium sarcosinate is adjusted to 1:4 to 4:1.

9. The process of claim 8 wherein the mole ratio of cyanamide to sodium or potassium sarcosinate is 0.9:1 to 1.25:1.

10. The process of claim 1 wherein the sodium or potassium sarcosinate is used as a 35 to 45 wt.-% aqueous solution.

11. The process of claim 1 wherein the cyanamide is in the form of an aqueous solution.

12. The process of claim 11 wherein the cyanamide is in the form of a 50 wt.-% aqueous solution.

13. The process of claim 1 wherein the organic solvent is an aliphatic alcohol containing 1 to 5 carbon atoms.

14. The process of claim 1 further comprising purifying the reaction product.

15. The process of claim 14 wherein the reaction product is purified by treatment with water.

16. The process of claim 1 wherein the reaction product is recrystallized from water.

17. The process of claim 1 wherein the reaction product is dried to a water content of <1 wt.-% for the preparation of anhydrous creatine.

18. The process of claim 1 wherein the reaction product is dried to a water content of about 12.1 wt.-% for the preparation of creatine monohydrate.

19. The process of claim 15 wherein the water is hot or cold water.

20. A process for the preparation of creatine or creatine monohydrate, comprising adding cyanamide to a solution of at least one of sodium sarcosinate or potassium sarcosinate in water or a mixture of water and an organic solvent and reacting the cyanamide with the sodium or potassium sarcosinate at a temperature of from 20° to 150° C. and a pH value of from 7.0 to 14.0.

* * * * *

UNITED STATES PATENT AND TRADEMARK OFFICE
CERTIFICATE OF CORRECTION

PATENT NO. : 5,719,319
DATED : February 17, 1998
INVENTOR(S) : Weiss et al.

It is certified that error appears in the above-identified patent and that said Letters Patent is hereby corrected as shown below:

On the title page, item[57], line 4 change ""en" to --an--.

In column 1, line 22, change "D" to --1--.

In column 1, line 33, after the second occurrence of "creatine" add --monohydrate--.

In column 1, line 51, change "with" to --in--.

In column 2, line 2, after "100°C" add --,--.

In column 2, line 44, change "a" to --an--.

In column 3, line 19, delete "is recommended".

In column 3, line 20, after "pressure" add --is recommended--.

In column 3, line 66, after "15°C" add --,--.

UNITED STATES PATENT AND TRADEMARK OFFICE
CERTIFICATE OF CORRECTION

PATENT NO. : 5,719,319
DATED : February 17, 1998
INVENTOR(S) : Weiss et al.

It is certified that error appears in the above-identified patent and that said Letters Patent is hereby corrected as shown below:

In column 4, line 30, change "crestinie" to --creatinine--.

In column 4, line 38, change "take" to --taken--.

In column 4, line 54, change "88.12%" to --88.2%--.

In column 4, line 59, change "674.5" to --674.8--.

In additional: Col.4, line 8, "EXAMPLE 5" should read --EXAMPLE 3"

Signed and Sealed this

Twentieth Day of July, 1999

Attest:

Q. TODD DICKINSON

*Attesting Officer*     *Acting Commissioner of Patents and Trademarks*